(12) United States Patent
Shukla

(10) Patent No.: US 6,432,438 B1
(45) Date of Patent: Aug. 13, 2002

(54) BIODEGRADABLE VEHICLE AND FILLER

(76) Inventor: Atul J. Shukla, 837 Walnut Bend Rd., Cordova, TN (US) 38018

(*) Notice: Subject to any disclaimer, the term of this patent is extended or adjusted under 35 U.S.C. 154(b) by 0 days.

(21) Appl. No.: 09/605,661

(22) Filed: Jun. 28, 2000

Related U.S. Application Data (63) Continuation of application No. 09/181,515, filed on Oct. 28, 1998.
(60) Provisional application No. 60/063,680, filed on Oct. 29, 1997.

(51) Int. Cl.[7] ............ A61F 13/00; A61F 2/00; A61K 9/22

(52) U.S. Cl. .......... 424/426; 424/423; 424/422; 424/400; 604/890.1

(58) Field of Search .............. 424/426, 423, 424/422, 400; 604/890.1

(56) References Cited

U.S. PATENT DOCUMENTS

| | | | | |
|---|---|---|---|---|
| 4,343,787 A | * | 8/1982 | Katz | 424/78 |
| 4,938,763 A | | 7/1990 | Dunn et al. | |
| 5,324,519 A | * | 6/1994 | Dunn et al. | 424/426 |
| 5,324,520 A | * | 6/1994 | Dunn et al. | 424/435 |
| 5,340,849 A | * | 8/1994 | Dunn et al. | 523/113 |
| 5,487,897 A | * | 1/1996 | Polson et al. | 424/426 |
| 5,525,646 A | * | 6/1996 | Lundgren et al. | 523/105 |
| 5,632,727 A | | 5/1997 | Tipton | |
| 5,660,849 A | | 8/1997 | Polson | |
| 6,130,200 A | | 10/2000 | Brodbeck et al. | |

OTHER PUBLICATIONS

F. Billmeyer, Jr., Textbook of Polymer Science, p. 472 John Wiley and Sons, New York, 1984.

Alfred Martin Physical Pharmacy, p. 588 Lea and Febiger, Philadelphia, 1993.

* cited by examiner

Primary Examiner—Thurman K. Page
Assistant Examiner—Todd D Ware (57) ABSTRACT

A biodegradable vehicle and filler (referred to in this invention as biodegradable vehicle), which can be mixed with one or more biologically active substances (BAS), or can be used as a biodegradable filler to fill in cavities or body tissues in animals, birds and humans. The consistency and rheology, hydrophilicity and hydrophobicity, and in vivo degradation rates of the biodegradable vehicle is controlled by modulating the molecular weight of polymers and copolymers, concentration of plasticizers, ratios of two or more plasticizer in the blends, types of polymers and copolymers, copolymer ratios, and ratios of blends of polymers with different molecular weights or different copolymers. The biodegradable vehicle is mixed with one or more BAS (which is separately stored away from the biodegradable vehicle in an appropriate container) just prior to use. Mixing of the BAS with the biodegradable vehicle can be accomplished by simply stirring the mixture with a stirring device, or by triturating the mixture or employing an ointment mill or a suitable device or apparatus or equipment that can be used for blending/mixing. Alternatively, a device, which resembles two syringes, attached together with a removable partition or a valve assembly can also be used to uniformly mix the BAS with the biodegradable vehicle. The mixing is performed in order to dissolve or uniformly suspend the BAS particles in the biodegradable vehicle. Modulating the polymer to plasticizer ratio, polymer molecular weight, copolymer ratio, and hydrophobicity and hydrophilicity of the plasticizer controls the release of the BAS from the biodegradable vehicle.

68 Claims, 2 Drawing Sheets

FIGURE 1a

BIODEGRADABLE POLYMERS
Polylactic acid (PLA)
Polylactic-co-glycolic acid (PLGLA)
Polyaminoacids
Polyhydroxybutyric and
Valeric acid copolymers (PHBV)
Poly-ε-caprolatone (PCL)
Lactic acid and caprolactone copolymers

VOLATILE SOLVENTS
Acetone
Ethyl acetate
Chloroform
Methyl acetate
Methylene chloride
Methylethyl ketone

↓

SOLUTION OF POLYMER IN VOLATILE SOLVENT(S)
+
PLASTICIZER

Citrates such as diethyl citrate (DEC), triethyl citrate (TEC), acetyl triethyl citrate (ATEC), tributyl citrate (TBC), acetyl tributyl citrate (ATBC), phthalates such as dimethyl phthalate (DMP), diethyl phthalate (DEP), triethyl phthalate (TEP), dibutyl phthalate (DBP), dioctyl phthalate, glycol ethers such as ethylene glycol diethyl ether, propylene glycol monomethyl ether, ethylene glycol monoethyl ether, diethylene glycol monoethyl ether (Transcutol®), propylene glycol monotertiary butyl ether, dipropylene glycol monomethyl ether, n-methyl pyrrolidone, 2 pyrrolidone (2-Pyrrol®), propylene glycol, glycerol, glyceryl dioleate, ethyl oleate, benzylbenzoate, glycofurol, sorbitol, sucrose acetate isobutyrate, butyryltri-n-hexyl-citrate, acetyltri-n-hexyl citrate, sebacates such as dibutyl sebacate, tributyl sebacate, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PEG), glycerol and PEG esters of acids and fatty acids (Gelucires®, Labrafils® and Labrasol®) such as PEG-6 glycerol mono oleate, PEG-6 glycerol linoleate, PEG-8 glycerol linoleate, PEG-4 glyceryl caprylate/caprate, PEG-8 glyceryl caprylate/caprate, polyglyceryl-3-oleate, polyglyceryl-6-dioleate, polyglyceryl-3-isostearate, PEG-32 glyceryl laurate (Gelucire 44/1®), PEG-32 glyceryl palmitostearate (Gelucire 50/13®), PEG-32 glyceryl stearate (Gelucire 53/10®), glyceryl behenate, cetyl palmitate, glyceryl di and tri stearate, glyceryl palmitostearate, and glyceryl triacetate (Triacetin®). vegetable oils obtained from seeds, flowers, fruits, leaves, stem or any part of a plant or tree including cotton seed oil, soy bean oil, almond oil, sunflower oil, peanut oil, sesame oil. The use of two or more plasticizers in a combination or blend of varying ratios and hydrophilicity or hydrophobicity is also encompassed by the present invention.

↓

SOLUTION OF POLYMER + PLASTICIZER IN VOLATILE SOLVENT(S)

↓

HEAT AND/OR APPLY VACUUM TO EVAPORATE THE VOLATILE SOLVENT

↓

BIODEGRADABLE VEHICLE AND FILLER

This application is a continuation in part of application Ser. No. 09/181,515 which was filed on Oct. 28, 1998. This application has just been allowed. The provisional application No. 60/063,680 and was filed on Oct. 29, 1997.

FIELD OF INVENTION

The present invention relates to a biodegradable vehicle and filler (referred to in this invention as biodegradable vehicle), which can be mixed with one or more biologically active substances (BAS), or can be used as a biodegradable filler to fill in cavities or body tissues in animals, birds and humans. The consistency and rheology, hydrophilicity and hydrophobicity, and in vivo degradation rates of the biodegradable vehicle is controlled by modulating the molecular weight of polymers and copolymers, concentration of plasticizers, ratios of two or more plasticizer in the blends, types of polymers and copolymers, copolymer ratios, and ratios of blends of polymers with different molecular weights or different copolymers. The biodegradable vehicle is mixed with one or more BAS (which is separately stored away from the biodegradable vehicle in an appropriate container) just prior to use. Mixing of the BAS with the biodegradable vehicle can be accomplished by simply stirring the mixture with a stirring device, or by triturating the mixture or employing an ointment mill or a suitable device or apparatus or equipment that can be used for blending/mixing. Alternatively, a device, which resembles two syringes, attached together with a removable partition or a valve assembly can also be used to uniformly mix the BAS with the biodegradable vehicle. The mixing is performed in order to dissolve or uniformly suspend the BAS particles in the biodegradable vehicle. Modulating the polymer to plasticizer ratio, polymer molecular weight, copolymer ratio, and hydrophobicity and hydrophilicity of the plasticizer controls the release of the BAS from the biodegradable vehicle.

BACKGROUND OF THE INVENTION

Biodegradable polymers refer to those polymers and copolymers that are slowly converted to nontoxic degradation products in the body. Examples include homopolymers and copolymers of polylactic acid (PLA), polyglycolic acid, polycaprolactone (PCL), polyanhydrides, polyorthoesters, polyaminoacids, pseudopolyaminoacids, polyhydroxybutyrates, polyhydroxyvalerates, polyphophazenes, polyalkylcyanoacrylates. These polymers have been used to prepare drug delivery systems such as microspheres and microcapsules (Schindler A, Jeffcoat R, Kimmel G L, Pitt C G, Wall M E and Zwelinger R., in: Contemporary Topics in Polymer Science, Pearce E M and Schaefgen J R, eds., Vol. 2, Plenum Publishing Corporation, New York, pp. 251–289, 1977; Mason N S, Gupta D V S, Keller, D W, Youngquist R S, and Sparks R F. Biomedical applications of microencapsulation, (Lim F, ed.), CRC Press Inc., Florida, pp. 75–84, 1984; Harrigan S E, McCarthy D A, Reuning R and Thies C., Midl. Macromol. Monograph, 5:91–100, 1978.; Sanders L M, Burns R, Bitale K and Hoffinan P., Clinical performance of nafarelin controlled release injectable: influence of formulation parameters on release kinetics and duration of efficacy., Proceedings of the International Symposium on Controlled Release and Bioactive Materials, 15:62–63, 1988; Mathiowitz E, Leong K and Langer R., Macromolecular drug release from bioerodible polyanhydride microspheres, in: Proceedings of the 12th International Symposium on Controlled Release of Bioactive Materials, Peppas N and Haluska R, eds., pp. 183, 1985), films (Jackanicz T M, Nash H A, Wise D L and Gregory J B. Polylactic acid as a biodegradable carrier for contraceptive steroids., Contraception, 8:227–233, 1973.; Woodland J H R, Yolles S, Blake A B, Helrich M and Meyer F J. Long-acting delivery systems for narcotic antagonist. I. J. Med. Chem., 16:897–901, 1973), fibers (Eenink M J D, Maassen G C T, Sam A P, Geelen J A A, van Lieshout J B J M, Olijslager J, de Nijs H, and de Jager E. Development of a new long-acting contraceptive subdermal implant releasing 3-ketodesogeatrel., Proceedings of the 15th International Symposium on Controlled Release of Bioactive Materials, Controlled Release Society, Lincolnshire, Ill. pp. 402403, 1988), capsules (Sidman K R, Schwope A D, Steber W D, Rudolph S E, Paulin S B. Biodegradable, implantable sustained release systems based on glutamic acid copolymers. J. Membr. Sci., 7:277–291, 1980; Pitt C G, Gratzl M M, Jeffcoat M A, Zweidinger R and Schindler A. Sustained drug delivery systems II: Factors affecting release rates from poly-□-caprolactone and related biodegradable polyesters., J. Pharm. Sci., 68(12):1534–1538, 1979), discs (Cowsar D R, Dunn R L., Biodegradable and non-biodegradable fibrous delivery systems, in: Long acting Contraceptive Delivery Systems, Zatuchni G I, Goldsmith A, Shelton J D and Sciarra J J, eds., Harper & Row, Publishers, Philadelphia, pp. 145–148, 1984), wafers (Brem et al., J. Neurosurgery, 74:441–446, 1991), and solutions (Dunn et al., U.S. Pat. No. 4,938,763; 5,324,519; 5,324,520; 5,278,201; 5,340,849; 5,368,859; 5,660849; 5,632,727; 5,599,552; 5,487,897). However, all these systems have at least one BAS, which is incorporated into the drug delivery system during the manufacture of dosage forms. Hence, these dosage forms have severe limitations in that, drug loading within a drug delivery system cannot be easily changed because the BAS is already incorporated into the drug delivery system at the time of manufacturing. Moreover, occasionally, there exists a possibility where a certain percentage of the BAS often degrades because of its exposure to the solvents, chemicals or other harsh manufacturing conditions during the preparation of the drug delivery system. Therefore, there clearly exists a need for developing a more versatile system where the BAS-loading (dose of BAS) can be tailored just prior to use, and the stability of the BAS can be enhanced.

SUMMARY OF THE PRESENT INVENTION

The present invention relates to methods for preparing a biodegradable vehicle. It also describes the composition of the biodegradable vehicle and the process of blending one or more BAS with the biodegradable vehicle just prior to its use. Keeping the BAS separated from the biodegradable vehicle can enhance the stability of the BAS. Moreover, the dose of BAS (BAS-loading) can be tailored by varying the ratio of the biodegradable vehicle to the BAS. An appropriate quantity of one or more BAS, as required by the end user, is blended with the biodegradable vehicle just prior to use. Mixing of the BAS with the biodegradable vehicle can be accomplished by simply stirring the mixture with a stirring device, or by triturating the no mixture or employing an ointment mill or a suitable device or apparatus or equipment that can be used for blending/mixing. Alternatively, a device, which resembles two syringes or syringe-like devices (e.g. pumps in which materials can be mixed by depressing a trigger-like device) attached together with a removable partition or a valve assembly can also be used to uniformly mix the BAS with the biodegradable vehicle. The BAS is loaded in one syringe or compartment and the biodegradable vehicle is loaded in the other compartment. A removable partition or a valve, which will allow the contents of the two compartments to be mixed uniformly, separates the two compartments. The mixing process is performed in order to dissolve or uniformly suspend the BAS particles in the biodegradable vehicle. The biodegradable vehicles can be free-flowing or viscous liquid, gel or paste. The method of manufacturing the biodegradable vehicle described in the present invention involves dissolving one or more biodegradable polymers and one or more plasticizers in a volatile solvent or mixture of volatile solvents. The volatile solvent is then removed using vacuum or evaporated at an elevated temperature, or removed using both vacuum and elevated temperature. The biodegradable vehicle could be sterilized in the final packaging by an appropriate technique including irradiation sterilization technique. Alternatively, the biodegradable vehicle can be prepared from pre-sterilized components in an aseptic environment. Sterilization of the solvents and plasticizers used in the manufacturing process could be accomplished by an appropriate sterilization technique such as filtration, autoclaving or irradiation. The sterilized biodegradable vehicle is blended with appropriate quantities of one or more BAS just prior to its use.

Advantages of the biodegradable vehicle described in the present invention include the flexibility of tailoring the dose of the BAS in the system by blending the requisite amount of BAS and the biodegradable vehicle just prior to its use, and enhancing stability of the BAS since it is blended with the biodegradable vehicle just prior to its use. A major reason for the enhanced stability of the BAS is that the BAS is not subjected to exposure to solvents, chemicals or the harsh processing conditions during the manufacture of the biodegradable vehicle. Moreover, the BAS is stored in an appropriate separate container; hence it does not come in contact with the biodegradable vehicle until it is blended with the vehicle just prior to use.

The biodegradable vehicle without blending any BAS may be used as a tissue or cavity filler or spacer in the body, whereas the biodegradable vehicle blended with the BAS just prior to its use may be used for the treatment of a variety of diseases and pathological conditions. The final composition with or without the BAS may be injected, implanted or applied directly to tissues in animals, birds and humans.

DETAILED DESCRIPTION OF THE INVENTION

The present invention relates to the process of preparing a biodegradable vehicle comprising of at least one polymer and one plasticizer. Appropriate quantities of the vehicle can then be blended with appropriate quantities of at least one BAS just prior to its use.

According to the present invention, the term polymer includes oligomer, copolymer and terpolymer. Biodegradable polymers are used in this invention because they form vehicles that can degrade in vivo into non-toxic degradation products. Moreover, these polymers are available in varying physicochemical properties including varying hydrophilicity and hydrophobicity, varying molecular weights, varying crystallinity and amorphous states and varying copolymer ratios. Tailoring either the degradation kinetics of the biodegradable vehicle or the release characteristics of the BAS from the BAS-loaded biodegradable vehicle can be easily achieved by varying several factors including, the consistency or rheology of the vehicle, BAS-loading, polymer molecular weight, hydrophilicity or hydrophobicity of the plasticizer, copolymer ratio, polymer to plasticizer ratio.

Plasticizers of varying hydrophilicities and hydrophobicities are used in the present invention in varying ratios in order to convert a polymer in a solid state to a biodegradable vehicle of varying consistency ranging from free-flowing or viscous liquid, a gel or a paste. Plasticizers are chemicals added to polymers to improve their flow, and therefore their processibility (Billmeyer, F., Jr. Textbook of Polymer Science, John Wiley and Sons, New York, 1984, p. 472). This is achieved by lowering their glass transition temperature (a temperature at which a glassy polymer becomes rubbery on heating and a rubbery polymer reverts to a glassy one on cooling), thus achieving a change in properties. A plasticizer can only plasticize a polymer when the molecules of the plasticizer can interact with the molecules of the polymer. Hence, the plasticizers act as lubricants between the polymer chains, facilitating slippage of chain past chain under stress and extending the temperature range for segmental rotation to lower temperatures (Martin, A., Physical Pharmacy, Lea and Febiger, Philadelphia, 1993, p. 588). The degree or extent of plasticization of a polymer will depend on the amount of plasticizer blended with the polymer. Higher the concentration of the plasticizer, greater the extent of plasticization or flexibility of the polymer. If a plasticizer and a polymer are fully compatible with each other, then depending on the concentration of the plasticizer blended with the polymer, it is possible to obtain a polymer matrix of varying consistency or rheology such as a free-flowing or viscous liquid, gel or paste. Moreover, since plasticizers are available with varying physicochemical properties, including varying hydrophilicity and lipophilicity, it is possible to blend an appropriate plasticizer at a desired concentration with a selected compatible polymer such that the resulting polymer matrix has the tailored physicochemical characteristics, including varying hydrophilicity and lipophilicity, and consistency. The present invention also includes formulations wherein two or more plasticizers are used in a combination or blend of varying ratios. Two or more polymers with different molecular weights and/or copolymer ratios or different types of polymer with varying crystallinity or hydrophobicity can also be blended with the plasticizer or combinations of two or more plasticizers to obtain biodegradable vehicle with unique consistency and rheology, degradation characteristics, hydrophilicity and hydrophobicity, depending on the type of polymer and plasticizer combination used in the preparation of the biodegradable vehicle. The release characteristics of the BAS from a BAS-loaded biodegradable vehicle can also be tailored by the aforementioned characteristics of the polymers and plasticizers in the biodegradable vehicle.

The present invention relates to methods for preparing a biodegradable vehicle. It also describes the composition of the biodegradable vehicle and the process of blending one or more BAS with the biodegradable vehicle just prior to its use. The BAS loading can be varied by varying the ratio of the biodegradable vehicle to the BAS. Moreover, keeping the BAS separated from the biodegradable vehicle in the present invention can enhance the stability of the BAS. The BAS is blended with the biodegradable vehicle just prior to use. The biodegradable vehicle can be free-flowing or viscous liquids, gels or pastes. The method of manufacturing the biodegradable vehicle described in the present invention involves dissolving one or more biodegradable polymers and one or more plasticizers in a volatile solvent or mixture of volatile solvents. The volatile solvent is then removed using vacuum or evaporated at an elevated temperature, or removed using both vacuum and elevated temperature.

The biodegradable vehicle could be sterilized in the final packaging by an appropriate technique including irradiation sterilization technique. Alternatively, the solution of the biodegradable polymer and plasticizer in the volatile solvent can be sterilized by an appropriate sterilization technique such as filtration. The volatile solvent is then removed from the resulting sterile solution using vacuum or evaporated at an elevated temperature, or removed using both vacuum and elevated temperature using an appropriate apparatus such as a rotary evaporator (Rotavap) fitted with pre-sterilized components, to yield sterile biodegradable vehicle. Sterile biodegradable vehicle can also be prepared from pre-sterilized components in an aseptic environment. Sterilization of the solvents and plasticizers used in the manufacturing process could be accomplished by an appropriate sterilization technique such as filtration or autoclaving or irradiation. The sterilized biodegradable vehicle is then stored in an appropriate container such as an ointment jar, ointment tube, vial, ampule or syringe until it is blended with appropriate quantities of one or more BAS (which is stored in another appropriate container separated from the biodegradable vehicle) just prior to its use. The sterile biodegradable vehicle can be used as biodegradable filler to fill cavities or tissues in the body.

Polymers suitable for preparing the biodegradable delivery systems of the present invention include, but are not limited to, polyesters, polyorthoesters, polyanhydrides, polyaminoacids, pseudopolyamino acids, polyamides, polyalkylcyanoacrylates, and polyphosphazenes. In a preferred embodiment, polymers include polylactic acid (PLA) and its copolymers (polylactic-co-glycolic acid or PLGA), polyglycolic acid and its copolymers, polycaprolactone (PCL) and its copolymers, polyhydroxybutyrates and their copolymers, and polyhydroxyvalerates and their copolymers. A mixture of polymers may be used to tailor either the release characteristics of BAS in the biodegradable delivery system, or the degradation characteristics of the biodegradable delivery system or both.

Solvents used to dissolve the polymer for the preparation of biodegradable delivery system of the present invention include, but are not limited to, ketones, ethers, alcohols, amides, and chlorinated solvents. Preferred solvents are acetone, ethyl acetate, methyl acetate, methylethylketone, chloroform, methylene chloride, isopropanol, ethyl alcohol, ethyl ether, methylethyl ether, hexafluroisopropanol, tertrahydrofuran, and hexafluroacetone sesquihydrate. A mixture of volatile solvents may also be used to create a suitable mixture, which can dissolve both the polymer and the plasticizer.

Plasticizers used for the preparation of biodegradable delivery system of the present invention include, but are not limited to, citrates such as:diethyl citrate (DEC), triethyl citrate (TEC), acetyl triethyl citrate (ATEC), tributyl citrate (TBC), acetyl tributyl citrate (ATBC), phthalates such as dimethyl phthalate (DMP), diethyl phthalate (DEP), triethyl phthalate (TEP), dibutyl phthalate (DBP), dioctyl phthalate, glycol ethers such as ethylene glycol diethyl ether, propylene glycol monomethyl ether, ethylene glycol monoethyl ether, diethylene glycol monoethyl ether (Transcutol®), propylene glycol monotertiary butyl ether, dipropylene glycol monomethyl ether, n-methyl pyrrolidone, 2 pyrrolidone (2-Pyrrol®), propylene glycol, glycerol, glyceryl dioleate, ethyl oleate, benzylbenzoate, glycofurol sorbitol sucrose acetate isobutyrate, butyryltri-n-hexyl-citrate, acetyltri-n-hexyl citrate, sebacates such as dibutyl sebacate, tributyl sebacate, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PEG), glycerol and PEG esters of acids and fatty acids (Gelucires®, Labrafils® and Labrasol®) such as PEG-6 glycerol mono oleate, PEG-6 glycerol linoleate, PEG-8 glycerol linoleate, PEG-4 glyceryl caprylate/caprate, PEG-8 glyceryl caprylate/caprate, polyglyceryl-3-oleate, polyglyceryl-6-dioleate, polyglyceryl-3-isostearate, PEG-32 glyceryl laurate (Gelucire 44/1®), PEG-32 glyceryl palmitostearate (Gelucire 50/13®), PEG-32 glyceryl stearate (Gelucire 53/10®), glyceryl behenate, cetyl palmitate, glyceryl di and tri stearate, glyceryl palmitostearate, and glyceryl triacetate (Triacetin®), vegetable oils obtained from seeds, flowers, fruits, leaves, stem or any part of a plant or tree including cotton seed oil, soy bean oil almond oil, sunflower oil, peanut oil, sesame oil. The use of two or more plasticizers in a combination or blend of varying ratios and hydrophilicity or hydrophobicity is also encompassed by the present invention.

Examples of BAS include, but are not limited to, steroids, hormones, antipsychotic agents, agents that act on the central nervous system (CNS-agents), fertility regulating agents, antibodies, antigens, anesthetics, analgesics, antibiotics, antiviral agents, antineoplastic agents, antifungal agents, cavity and infection preventing agents, cardiovascular agents, antinflammatory agents, vasodilators, brochiodilators, alkaloids, peptides and proteins, vaccines, live or killed bacteria or viruses, growth promoting agents, natural tissues such as bones or agents derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues and organs.

Advantages of the biodegradable vehicle described in the present invention include the flexibility of tailoring the BAS loading in the system by blending the requisite amount of one or more BAS and the biodegradable vehicle just prior to its use, and enhancing stability of the BAS since it is blended with the biodegradable vehicle just prior to its use. Another major reason for the enhanced stability of the BAS is that the BAS is not subjected to exposure to solvents, chemicals or the harsh processing conditions during the manufacture of the biodegradable vehicle. Moreover, the BAS is stored in an appropriate separate container; hence it does not come in contact with the biodegradable vehicle until it is blended with the vehicle just prior to use. The BAS can be present either in the solid state, liquid state (where the BAS is dissolved in the plasticizer or blends of plasticizers), or as a suspension (where the BAS is suspended in the plasticizer or blends of plasticizers) in an appropriate container separated from the biodegradable vehicle. The BAS could also be present in the dissolved or a suspended state in a viscous liquid, semi-solid or gel or a paste form of a plasticizer or blends of plasticizers in a separate container.

After an appropriate quantity of the BAS is added to the biodegradable vehicle, the BAS-loaded vehicle may be free-flowing or a viscous solution or suspension wherein the BAS is either dissolved or suspended in the free-flowing or viscous polymer-plasticizer blended liquids, or gels with dissolved or suspended BAS, or pastes with dissolved or suspended BAS. The consistency or rheology, physico-chemical properties of the biodegradable vehicle and the physical form of the BAS-loaded biodegradable vehicle (i.e. a solution in which the BAS is completely dissolved or a suspension where the BAS is suspended in the biodegradable vehicle), rate and duration of in vivo biodegradation, and BAS release characteristics from the biodegradable vehicle depend on a number of factors. These include: physicochemical properties of polymers such as type, molecular weight, glass-transition temperature, hydrophilicity and lipophilicity; physicochemical properties of plasticizer such as type, hydrophilicity and lipophilicity, boiling point or[]melting point; and physicochemical properties of BAS such as type, hydrophilicity and lipophilicity, molecular weight, melting point or boiling point. In addition, polymer, plasticizer or BAS concentration in the biodegradable vehicle, and the physicochemical interactions between the polymer, plasticizer and BAS also affect the rate and duration of in vivo biodegradation, and BAS release characteristics. For example, using the present invention, it is possible to tailor the release of a BAS (with specific physicochemical properties and the desired in vivo concentration), for the desired length time. This is achieved by blending an appropriately selected polymer or blends of different polymers or copolymers with an appropriately selected plasticizer or mixtures of plasticizers. Besides controlling the release characteristics of the BAS from the delivery system described in the present invention, an appropriate blend of the polymer and plasticizer also controls the consistency and rheology of the delivery system It is also possible to extend the in vivo duration of stay of the delivery system by selecting a higher molecular weight polymer, since polymers with higher molecular weights generally degrade slowly in the body. Alternatively, it is possible to modify the degradation kinetics of the biodegradable vehicle or obtain pulsatile or intermittently fluctuating delivery of the BAS from the BAS-loaded biodegradable vehicle by combining polymers of different molecular weights (e.g. low, intermediate and high molecular weights or low and high molecular weights or low and medium molecular weights or medium and high molecular weights), whereby the low molecular weight polymer in the biodegradable vehicle may degrade at a much faster rate than the rest of the polymer in the blend. Alternatively, using blends of copolymers of different copolymer ratios of varying hydrophilicity and hydrophobicity (e.g. different copolymer ratio of lactide-glycolide or lactide-caprolactone) or using blends of two different polymers or copolymers with different crystallinity (e.g. blends of polyacaprolactone and polylactic acid or polycaprolactone and poly-lactic-co-glycolic acid) can also result in a biodegradable vehicle with varying degradation kinetics where the more hydrophilic or amorphous polymer may degrade at a much faster rate than the rest of the polymers in the blend. The biodegradable vehicle without blending any BAS may be used as a tissue or cavity filler or spacer in the body, whereas the biodegradable vehicle blended with the BAS just prior to its use may be used for the treatment of a variety of diseases and pathological conditions. The final composition with or without the BAS may be injected, implanted or applied directly to tissues in animals, birds and humans.

Figure 1B:
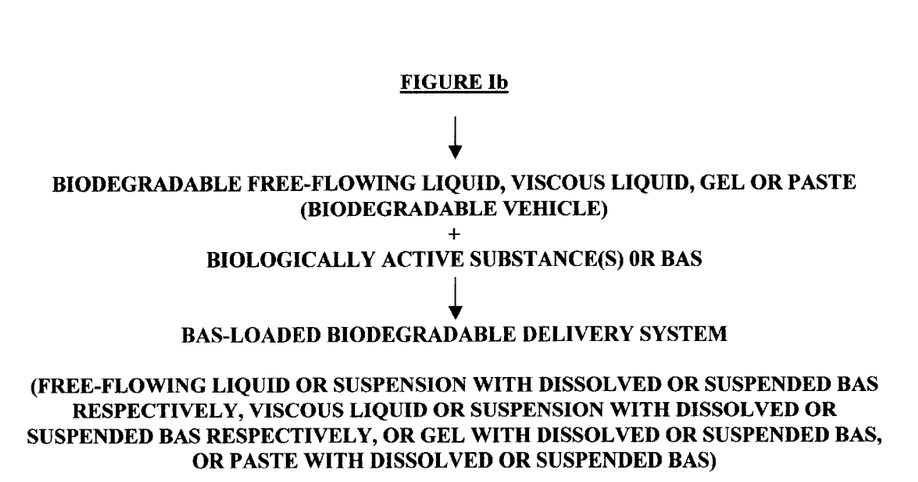
FIG. 1 shows a method of preparing a biodegradable vehicle.

Methods of preparing the biodegradable vehicle of the present invention involve dissolving at least one biodegradable polymer in a volatile solvent or a mixture of solvents. The biodegradable vehicle of the present invention is prepared by dissolving at least one biodegradable polymer in a volatile solvent. Following this, at least one plasticizer is added to the polymer solution. This solvent is evaporated using vacuum or removed at an elevated temperature, or evaporated using a combination of both vacuum and elevated temperature, resulting in the formation of the biodegradable vehicle in the form of either free-flowing or viscous liquids, gels or pastes. BAS may next be added to the biodegradable vehicle just prior to its use to obtain a delivery system in the form of free-flowing or viscous liquid where the BAS is completely dissolved in the polymer-plasticizer blended free-flowing or viscous liquids or gels or pastes. BAS could also exist as a suspension in the free-flowing or viscous liquid or gels or pastes. This system provides controlled release of the BAS over the desired length of time. The procedure for preparing a biodegradable vehicle first, followed by a BAS-loaded delivery system is shown in FIG. 1.

The biodegradable vehicle may be used as a biodegradable tissue or cavity filler or spacer in the body, whereas, BAS-loaded biodegradable vehicle may be used for the treatment of a variety of diseases and pathological conditions. The BAS-loaded vehicle may be injected, implanted or applied in animals and humans. This unique form of drug delivery system offers distinct advantages in certain types of treatment where the dose of the BAS has to be individualized, and site-specific delivery of the BAS is needed. Hence, as a result, the BAS has to be blended with the biodegradable vehicle just prior to injection, implantation or application at the site of administration. Occasionally, more than one type of BAS could be loaded in the biodegradable vehicle in order to treat certain disease conditions. For example, the biodegradable vehicle loaded with an appropriate quantity of an antitumor agent can be injected directly into a solid tumor or at a site from where a solid tumor has been surgically removed. The BAS-loaded biodegradable vehicle can be prepared in a pharmacy or in an operating room by the health practitioner (a pharmacist, surgeon, nurse), just prior to administration to the patient. A similar treatment can be offered to patients with brain tumors where the biodegradable vehicle loaded with an appropriate quantity of an antitumor agent can be injected, implanted or applied directly at the site in the brain from where the tumor has been removed. BAS-loaded biodegradable vehicle can also be used in surgeries where appropriate quantities of an antibiotic, an anti-inflammatory agent, a local anesthetic or analgesic, or combinations thereof can be loaded in the biodegradable vehicle by the surgeon in an operating room, and the resulting mixture can then be injected, implanted, smeared or applied at the site of surgery to minimize the chances of localized infections or inflammation and reduce pain respectively, due to surgery. In the case of orthopedic surgery, currently, the majority of the orthopedic surgeons prepare beads loaded with an appropriate dose of an antibiotic with a non-biodegradable polymer, polymethylmethacrylate (PMMA) in the operating room. These beads are then placed in the cavity at the site of surgery to prevent infections such as osteomyelitis. However, the non-degradable polymer beads have to be eventually removed before closing the wound with a suture, and the patients are then given an intravenous dose of an antibiotic or treated with an oral antibiotic. This procedure can easily be corrected with the use of an antibiotic loaded biodegradable vehicle that can be injected, implanted, applied or smeared near or at the site of surgery. High concentrations of the antibiotic at the site of surgery can prevent infections. Moreover, the BAS delivery system need not be removed from the site of administration because of the biodegradable nature of the system The biodegradable vehicle loaded with bone growth promoting agents such as calcium sulfate, calcium carbonate, calcium phosphate or hydroxyapatite can be injected, implanted, applied or smeared at an appropriate site where it is needed following bone surgery. BAS such as low molecular weight heparin can also be incorporated into the biodegradable vehicle and the resulting mixture can be used to treat conditions such as deep venous thrombosis (DVT) in trauma or surgical patients.

The biodegradable vehicle could be loaded with a contraceptive agent, antipsychotic agent, anticonvulsants, antimalarial antihypertensive agent, antibiotics, antiviral agents, and biologically active protein and peptides, vaccines, live or killed bacteria or viruses, genes, DNA or DNA fragments and residues, and injected subcutaneously or intramuscularly or implanted or applied at the site of administration to provide a controlled release of the BAS for the desired length of time. Biodegradable vehicle loaded with BAS such as antiinflammatory agents, analgesics and anesthetics could be injected directly into joints or sites in the body from where the pain is emanating, thus providing relief from the excruciating pain and making the joints more mobile. Antigens may also be incorporated into the delivery system and injected, implanted or applied in animals or humans to induce the production of specific antibodies. Morphogenic proteins such as growth promoting agents of biological tissues and organs, wound-healing factors, bones, (fragments or powder) can also be incorporated into the biodegradable vehicle, and the resulting mixture is injected, implanted or applied at the site of administration. Whole or a part of a tissue or tissues and organs can also be blended with the biodegradable vehicle and injected, implanted or applied at the site of administration. For pulsatile or intermittent delivery of BAS such as vaccines, the biodegradable vehicle can be prepared with blends of varying molecular weights of polymers or copolymers, or with blends of copolymers of varying copolymer ratios (e.g. 50/50 PLGA and 85/15 PLGA or 100% PLA and 25/75 PLGA) or blends of different types of biodegradable polymers with varying hydrophobicity or lipophilicity or crystallinity (e.g. 1:1 of PLA:PCL or 1:3 of PLA:PCL or 1:1 of 50/50 PLGA:PCL).

This invention will be understood with greater particularity by reviewing the following examples:

EXAMPLES

Example 1

Preparation of a Biodegradable Vehicle

A polymer (50% w/w of 50/50 lactide-co-glycolide copolymer) was dissolved in minimum quantity of acetone. Triethyl citrate (TEC), at a concentration of 50% w/w, was added to the polymer solution and was stirred to yield a uniform mixture. Acetone was evaporated from the mixture by heating at 60–75° C. with constant stirring. The resulting biodegradable vehicle had a gel-like consistency.

Example 2

Example 1 was repeated using 10% w/w of 50/50 lactide-co-glycolide copolymer and 90% w/w TEC. The resulting biodegradable vehicle had a liquid-like consistency.

Example 3

Example 1 was repeated using 20% w/w of 50/50 lactide-co-glycolide copolymer and 80% w/w TEC. The resulting biodegradable vehicle had a viscous liquid-like consistency.

Example 4

Example 1 was repeated, using 30% w/w of 50/50 lactide-co-glycolide copolymer and 70% w/w TEC was used. The resulting biodegradable vehicle had a viscous liquid-like consistency.

Example 5

Example 1 was repeated, using 40% w/w of 50/50 lactide-co-glycolide copolymer and 60% w/w TEC was used. The resulting biodegradable vehicle had a viscous liquid-like consistency.

Example 6

Example 1 was repeated, using 60% w/w of 50/50 lactide-co-glycolide copolymer and 40% w/w TEC was used. The resulting biodegradable vehicle had a gel-like consistency.

Example 7

Example 1 was repeated, using 70%.w/w of 50/50 lactide-co-glycolide copolymer and 30% w/w TEC was used. The resulting biodegradable vehicle had a gel-like consistency.

Example 8

Example 1 was repeated, using 80% w/w of 50/50 lactide-co-glycolide copolymer and 20% w/w TEC was used. The resulting biodegradable vehicle was a thick sticky paste.

Example 9

Example 1 was repeated with the following polymers and plasticizers as shown in Table 1 below:

TABLE 1

| TYPE OF POLYMER | PLASTICIZER | SOLVENT | DESCRIPTION OF THE FORMULATION |
|---|---|---|---|
| DL-POLYLACTIC ACID (DL-PLA; I.V. = 0.58) | GLYCERYL TRIACETATE (TRIACETIN) | ACETONE | GEL, SLIGHTLY CLOUDY |
| DL-POLYLACTIC ACID (DL-PLA; I.V. = 0.58) | TRIETHYL CITRATE (TEC) | ACETONE | GEL, TRANSPARENT |
| DL-POLYLACTIC ACID (DL-PLA; I.V. = 0.58) | ACETYL TRIETHYL CITRATE (ATEC) | ACETONE | GEL, SLIGHTLY CLOUDY |
| DL-POLYLACTIC ACID (DL-PLA; I.V. = 0.58) | DIMETHYL PHTHALATE (DMP) | ACETONE | GEL, LESS VISCOUS, TRANSPARENT |
| DL-POLYLACTIC ACID (DL-PLA; I.V. = 0.58) | DIETHYL PHTHALATE (DEP) | ACETONE | GEL, TRANSPARENT |

TABLE 1-continued

| TYPE OF POLYMER | PLASTICIZER | SOLVENT | DESCRIPTION OF THE FORMULATION |
|---|---|---|---|
| DL-POLYLACTIC-CO-GLYCOLIC ACID (DL-PLGLA; I.V. = 0.58) | GLYCERYL TRIACETATE (TRIACETIN) | ACETONE | GEL, LESS VISCOUS, SLIGHTLY YELLOW |
| DL-POLYLACTIC-CO-GLYCOLIC ACID (DL-PLGLA; I.V. = 0.58) | TRIETHYL CITRATE (TEC) | ACETONE | GEL, SLIGHTLY YELLOW |
| DL-POLYLACTIC-CO-GLYCOLIC ACID (DL-PLGLA; I.V. = 0.58) | ACETYL TRIETHYL CITRATE (ATEC) | ACETONE | GEL, SLIGHTLY YELLOW |
| DL-POLYLACTIC-CO-GLYCOLIC ACID (DL-PLGLA; I.V. = 0.58) | TRIETHYL CITRATE (TEC) | ACETONE | GEL, SLIGHTLY YELLOW |
| DL-POLYLACTIC-CO-GLYCOLIC ACID (DL-PLGLA; I.V. = 0.58) | DIMETHYL PHTHALATE (DMP) | ACETONE | GEL, LESS VISCOUS, RANSPARENT |
| DL-POLYLACTIC-CO-GLYCOLIC ACID (DL-PLGLA; I.V. = 0.58) | DIETHYL PHTHALATE (DEP) | ACETONE | GEL, SLIGHTLY YELLOW |
| DL-POLYLACTIC-CO-GLYCOLIC ACID (DL-PLGLA; I.V. = 0.58) | N-METHYL PYRROLIDONE (NMP) | ACETONE | VISCOUS LIQUID, TRANSPARENT |
| DL-POLYLACTIC-CO-GLYCOLIC ACID (DL-PLGLA; I.V. = 0.15) | GLYCERYL TRIACETATE (TRIACETIN) | ACETONE | VISCOUS LIQUID, TRANSPARENT |
| DL-POLYLACTIC-CO-GLYCOLIC ACID (DL-PLGLA; I.V. = 0.15) | TRIETHYL CITRATE (TEC) | ACETONE | VISCOUS LIQUID, TRANSPARENT |
| DL-POLYLACTIC-CO-GLYCOLIC ACID (DL-PLGLA; I.V. = 0.15) | ACETYL TRIETHYL CITRATE (ATEC) | ACETONE | VISCOUS LIQUID, TRANSPARENT |
| DL-POLYLACTIC-CO-GLYCOLIC ACID (DL-PLGLA; I.V. = 0.15) | TRIETHYL CITRATE (TEC) | ACETONE | VISCOUS LIQUID, TRANSPARENT |

Example 10

Several polymers were separately dissolved in several volatile solvents. Several plasticizers were separately added to the polymer-solutions, such that the ratio of polymer to plasticizer in the final formulations ranged from 1:19 to 4:1. The solvents were then evaporated at an elevated temperature to obtain drug-loaded formulations. Several drugs were separately added to the biodegradable vehicle (polymer-plasticizer blends). The drug content in the final formulations constituted up to 50% w/w.

TABLE 2

| TYPE OF POLYMERS | PLASTICIZERS | SOLVENTS | POLYMER TO PLASTICIZER RATIOS | DRUGS | CONCENTRATION OF DRUGS (% w/w) IN POLYMER MATRICES |
|---|---|---|---|---|---|
| POLYCAPROLACTONE POLYLACTIC ACID | DIETHYLENE GLYCOL MONOETHYL ETHER (TRANSCUTOL ®), | METHYLENE CHLORIDE CHLOROFORM | 1:1 1:2 | TESTOSTERONE PROGESTERONE | 0.5%–50% w/w |
| POLYLACTIC-CO-GLYCOLIC ACID | PEG-8-GLYCERYL CAPRYLATE/CAPRATE (LABRASOL ®) | ACETONE | 1:3 | LEVONORGESTREL | |
| COPOLYMERS OF LACTIC ACID AND CAPROLACTONE | TRIETHYL CITRATE (TEC), ACETYL TRIETHYL CITRATE (ATEC) GLYCERYL TRIACETATE (TRIACETIN ®) POLYETHYLENE GLYCOLS (PEG) N-METHYL PYRROLIDONE (NMP) | ETHYL ACETATE | 1:4 1:9 1:19 2:1 2:3 3:2 3:1 4:1 | THEOPHYLLINE PROPRANOLOL ATENOLOL METOPROLOL CHLORPROAMAZINE CLONIDINE THEOPHYLLINE INSULIN OXYTETRACYCLINE NALTREXONE | |

Example 11

Effect of Varying Polymer-to-plasticizer Ratios on the Physical State of Formulations and Drug Release Characteristics Several samples of polylactic-co-glycolic acid (inherent viscosoty –0.59) were weighed and separately dissolved in acetone. Varying ratios of N-methyl pyrrolidone (NMP) were separately added to the polymer-solutions, such that the ratio of polymer to plasticizer in the formulations ranged from 20:80 to 80:20. Acetone was then evaporated by heating the solutions at 70–80° C. Levonorgestrel (2% w/w) was added to the resulting formulations. Table 3 describes the physical state of the formulations containing varying polymer-to-plasticizer ratios.

TABLE 3

Physical state of formulations containing varying polymer-to-plasticizer ratios

| Polymer*-to-NMP Ratio | Physical State of the Formulation | Physical State of Drug in the Formulation |
|---|---|---|
| 20:80 | Very flowable liquid | Dissolved |
| 40:60 | Viscous liquid | Dissolved initially; however precipitated partially after 48 hrs |
| 50:50 | Flowable gel | Suspended |
| 60:40 | Flowable gel | Suspended |
| 80:20 | Thick paste | Suspended |

*50/50 Polylactide-co-glycolide (IV = 0.59 dL/g)
Drug loading = 2% w/w

Example 12

Effect of Varying Polymer Inherent Viscosities on the Physical State of the Formulations and Drug Release Characteristics Several samples of polylactic-co-glycolic acid (PLGLA) with varying inherent viscosities ranging from 0.15–1.07 were weighed and separately dissolved in acetone. An appropriate quantity of N-methyl pyrrolidone (NMP) was added to the polymer-solutions such that the ratio of polymer to plasticizer In the formulations was 33% PLGLA and 67% NMP. Acetone was then evaporated by heating the solutions at 70–80° C. Levonorgestrel (2% w/w) was added to the resulting formulations. Table 4 describes the physical state of the formulations containing varying polymer inherent viscosities.

TABLE 4

Physical state of formulations containing varying polymer inherent viscosities

| Polymer Inherent Viscosity (dL/g) | Physical State of the Formulation* | Physical State of Drug in the Formulation* |
|---|---|---|
| 0.15 | Very flowable liquid | Dissolved |
| 0.26 | Flowable liquid | Dissolved |
| 0.42 | Flowable liquid | Dissolved |
| 0.59 | Viscous liquid | Dissolved |
| 0.74 | Flowable gel | Dissolved |
| 1.07 | Viscous gel | Dissolved |

*33% w/w of 50/50 Polylactide-co-glycolide and 67% w/w NMP
Drug loading = 2% w/w

Example 13

Effect of Varying Polymer Inherent Viscosities on Physical State of Formulations and Drug Release Characteristics Samples of pure polylactic acid and polylactic-co-glycolic acid (PLGLA) with varying copolymer ratios ranging from 50/50 to 85/15 were weighed and separately dissolved in acetone. An appropriate quantity of N-methyl pyrrolidone (NMP) was added to the polymer-solutions such that the ratio of polymer to plasticizer in the formulations was 33% PLGLA and 67% NMP. Acetone was then evaporated by heating the solutions at 70–80° C. Levonorgestrel (2% w/w) was added to the resulting formulations. Table 5 describes the physical state of the formulations prepared from varying copolymer ratios.

TABLE 5

Physical state of formulations containing varying copolymer ratios.

| Ratio of Lactide to Glycolide in Polymer | Physical State of the Formulation* | Physical State of Drug in the Formulation* |
|---|---|---|
| 50/50 | Yellowish, viscous liquid | Dissolved |
| 65/35 | Yellowish, viscous liquid | Dissolved |
| 75/25 | Pale yellow, highly viscous liquid | Dissolved |
| 85/15 | Straw colored, slightly translucent, highly viscous liquid | Dissolved |
| 100/0 | Clear, highly viscous liquid | Dissolved |

*33% w/w of 50/50 Polylactide-co-glycolide (IV = 0.59 dL/g) and 67% w/w NMP
Drug loading = 2% w/w

Example 14

Effect of Varying Drug Loadings on Drug Release

A polymer (25% w/w of 50/50 lactide-co-glycolide copolymer, inherent viscosity of 0.59) was dissolved in a minimum quantity of acetone. Pure polyethylene glycol 400 (PEG 400) was added to the polymer solution. The solution was stirred to yield a uniform mixture. Acetone was evaporated from the mixture by heating at 60–75° C. with constant stirring. The biodegradable vehicle was kept in a vacuum oven at 60–75° C. overnight to ensure complete removal of acetone. The resulting biodegradable vehicle had a viscous liquid like consistency. Three different concentrations of oxytetracycline base (either 10, 20 or 30% w/w) were added to the biodegradable vehicle and mixed thoroughly to ensure uniform distribution of the drug in the formulations. Drug release from the drug-loaded formulations was performed at 37° C. in isotonic phosphate buffer containing sodium sulfite as an antioxidant. Increasing he percentage of drug in the formulations from 10 to 30% w/w increased the cumulative amount of drug released. This increase occurred because, at higher drug-loadings, more drug is available at the surface of the formulations for the release. Moreover, a higher drug concentration gradient between the formulation and the dissolution medium is expected at 30% w/w drug-loading compared to the one at 10% w/w drug loading.

Example 15

Effect of Plasticizer Compositions on Drug Release

A polymer (25% w/w of 50/50 lactide-co-glycolide copolymer, inherent viscosity of 0.59) was dissolved in a minimum quantity of acetone. Either pure triethyl citrate (TEC), or polyethylene glycol 400 (PEG 400), or blends of PEG 400 and TEC (either 50/50% or 75/25% blends of PEG 400/TEC) was added to the polymer solution. The resulting solutions were stirred to yield uniform mixtures. Acetone was evaporated from the mixtures by heating at 60–75° C. with constant stirring. The biodegradable vehicles were kept in a vacuum oven at 60–75° C. overnight to ensure complete removal of acetone. The resulting biodegradable vehicles had a viscous liquid like consistency. Oxytetracycline base (20% w/w) was added to each biodegradable vehicle and mixed thoroughly to ensure uniform distribution of the drug in the formulations. Drug release from the drug-loaded biodegradable vehicles was performed at 37° C. in isotonic phosphate buffer containing sodium sulfite as an antioxidant. Increasing the percentage of PEG 400 in the formulations prepared from 0% PEG 400 and 100% TEC to 100% PEG 400 and 0% TEC resulted in faster drug release. This is because the PEG 400 is very hydrophilic and is completely miscible with water, whereas the aqueous solubility of TEC is approximately 6%.

Example 16

Effect of Varying Ratios of Polymer and Plasticizer on Drug Release

Three different concentrations (10, 20 and 25% w/w) of a polymer (50/50 lactide-co-glycolide copolymer, inherent viscosity of 0.59) were dissolved in a minimum quantity of acetone. Pure PEG 400 (90, 80 or 75%) was added to the polymer solutions. The solutions were stirred to yield uniform mixtures. Acetone was evaporated from the mixtures by heating at 60–75° C. with constant stirring. The biodegradable vehicles were kept in a vacuum oven at 60–75° C. overnight to ensure complete removal of acetone. The resulting biodegradable vehicles had varying viscosities or consistency. The formulation with 25% polymer was considerably more viscous than the one with 10% polymer. Oxytetracycline base (20% w/w) was added to each biodegradable vehicle and mixed thoroughly to ensure uniform distribution of the drug in the formulations. Drug release from the drug-loaded biodegradable vehicles was performed at 37° C. in isotonic phosphate buffer containing sodium sulfite as an antioxidant. Decreasing the percentage of polymer in the formulations from 25% to 10% dramatically increased the drug release. This is because a decrease in polymer concentration from 25% to 10% and a corresponding increase in the plasticizer concentration from 75% to 90% resulted in a decrease in the glass transition temperature, viscosity and an increase in polymer chain mobility of the formulations. Hence, the formulation with 10% polymer offered considerably less resistance for drug diffusion through the matrix compared to the one prepared with 25% polymer.

Example 17

Effect of Varying Plasticizer Hydrophilicity on Drug Release

A polymer (25% w/w of 50/50 lactide-co-glycolide copolymer, inherent viscosity of 0.59) was dissolved in a minimum quantity of acetone. Either pure polyethylene glycol 400, triethyl citrate (TEC) or acetyl triethyl citrate (ATEC) was added to the polymer solution. The resulting solutions were stirred to yield uniform mixtures. Acetone was evaporated from the mixtures by heating at 60–75° C. with constant stirring. The biodegradable vehicles were kept in a vacuum oven at 60–75° C. overnight to ensure complete removal of acetone. The resulting biodegradable vehicles had viscous liquid like consistency. Oxytetracycline base (20% w/w) was added to each biodegradable vehicle and mixed thoroughly to ensure uniform distribution of the drug in the formulations. Drug release from the drug-loaded biodegradable vehicles was performed at 37° C. in isotonic phosphate buffer containing sodium sulfite as an antioxidant. Drug release was fastest from formulations prepared with PEG 400, and slowest from those prepared with ATEC. Intermediate drug release was observed from formulations prepared from TEC. This is because PEG 400 is completely miscible with water, whereas, the solubility of TEC in water is approximately 6% and ATEC is almost insoluble in water with an aqueous solubility of less than 0.1%.

Example 18

Effect of Varying Polymer to Plasticizer Ratios and Plasticizer Compositions on Drug Release Biodegradable vehicles were prepared by dissolving either 16.67% w/w or 25% w/w of 50/50 polylactide-co-glycolide copolymer (inherent viscosity of 0.59) and either 50/50% or 75/25% blends of PEG 400 and TEC in a minimum quantity of acetone. The resulting solutions were stirred to yield uniform mixtures. Acetone was evaporated from the mixtures by heating at 60–75° C. with constant stirring. The biodegradable vehicles were kept in a vacuum oven at 60–75° C. overnight to ensure complete removal of acetone. The biodegradable vehicles had a viscous liquid like consistency. Oxytetracycline base (20% w/w) was added to each biodegradable vehicle and mixed thoroughly to ensure uniform distribution of the drug in the vehicles. Drug release from the drug-loaded biodegradable vehicles was performed at 37° C. in isotonic phosphate buffer containing sodium sulfite as an antioxidant. Faster drug release was observed from formulations prepared with a 16.67% polymer and 83.3% of plasticizer blends of varying compositions (polymer to plasticizer ratio of 1:5) compared to those prepared from formulations with polymer to plasticizer ratios of 1:3 (i.e. 33.3% polymer and 66.7% plasticizer). This is because increasing the polymer concentration in the formulations from 16.67% to 33.3% increased the viscosity of the formulations and decreased the drug diffusion from the formulations. Moreover, a comparison of drug released from formulations with similar polymer to plasticizer ratios but varying plasticizer compositions revealed that drug release was considerably faster from formulations prepared with blends of 75% PEG 400 and 25% TEC compared to those prepared from 50/50% blend of PEG 400/TEC. This is because the PEG 400 is completely miscible in water, whereas, the aqueous solubility of TEC in water is approximately 6%).

Example 19

Effect of Varying Polymer Inherent Viscosities on Drug Release

Four different inherent viscosities (i.v.=0.15, 0.26, 0.59 and 0.76) of a polymer (50/50 lactide-co-glycolide copolymer) were dissolved in a minimum quantity of acetone. Pure PEG 400 was added to the polymer solutions. The solutions were stirred to yield uniform mixtures. Acetone was evaporated from the mixtures by heating at 60–75° C. with constant stirring. The biodegradable vehicles were kept in a vacuum oven at 60–75° C. overnight to ensure complete removal of acetone. The resulting biodegradable vehicles had varying viscosities or consistency. The vehicle prepared with the polymer of inherent viscosity of 0.76 was considerably more viscous than the one prepared with the polymer of inherent viscosity of 0.15. Oxytetracycline base (20% w/w) was added to each biodegradable vehicle and mixed thoroughly to ensure uniform distribution of the drug in the formulations. Drug release from the drug-loaded formulations was performed at 37° C. in isotonic phosphate buffer containing sodium sulfite as an antioxidant. Decreasing the inherent viscosity of polymer from 0.76 to 0.15 dramatically increased the drug release. This is because a decrease in polymer inherent viscosity resulted in a dramatic decrease in the viscosity of the formulation and a corresponding decease in resistance to drug diffusion from the matrix.

Example 20

Effect of Varying Drug Solubility on Drug Release

Biodegradable vehicle was prepared by dissolving 25% of a polymer (50/50 lactide-co-glycolide copolymer, inherent viscosity of 0.64) and pure PEG 400 or 50/50% blends of PEG 400 and TEC in a minimum quantity of acetone. The solutions were stirred to yield a uniform mixture. Acetone was evaporated from the mixtures by heating at 60–75° C. with constant stirring. The biodegradable vehicles were kept in a vacuum oven at 60–75° C. overnight to ensure complete removal of acetone. The resulting biodegradable vehicles had viscous liquid-like consistency. Either hydrated naltrexone base (20% w/w) or naltrexone hydrochloride (20% w/w) was added to the biodegradable vehicles and mixed thoroughly to ensure uniform distribution of the drugs in the formulations. Drug release from the drug-loaded biodegradable vehicles was performed at 37° C. in isotonic phosphate buffer. The release of naltrexone hydrochloride was considerably faster from formulations prepared with both pure PEG 400 and 50/50% blends of PEG 400 and TEC than the release of the hydrated naltrexone base from similar formulations. This is because the solubility of the naltrexone hydrochloride in the dissolution buffer is much greater than that of the hydrated naltrexone base.

A similar drug release study was performed with formulations containing either 20% oxytetracycline hydrochloride or 20% oxytetracycline base. The blank formulations were prepared by dissolving 25% of a polymer (50/50 lactide-co-glycolide copolymer, inherent viscosity of 0.59) and 75% of pure PEG 400 in a minimum quantity of acetone. The solutions were stirred to yield a uniform mixture. Acetone was evaporated from the mixtures by heating at 60–75° C. with constant stirring. The biodegradable vehicles were kept in a vacuum oven at 60–75° C. overnight to ensure complete removal of acetone. The resulting biodegradable vehicles had viscous liquid-like consistency. Either 20% oxytetracycline hydrochloride or 20% oxytetracycline base was added to the resulting biodegradable vehicles and mixed thoroughly to ensure uniform drug distribution. Drug release from the drug-loaded biodegradable vehicles was performed at 37° C. in isotonic phosphate buffer containing sodium sulfite as an antioxidant. The release of oxytetracycline hydrochloride was considerably faster than the release of oxytetracycline base from similar formulations. This is because of the greater aqueous solubility of the hydrochloride salt than the base.

Example 21

Biodegradable delivery systems could be prepared by the procedures shown in Examples 1–20. Instead of adding a single biologically active agent, a combination of two or more biologically active agents could be incorporated together in the said delivery system. Examples of some of the combinations of the biologically active agents include levonorgestrel and ethinyl estradiol trimethoprim and sulfarnethoxazole, trimetrexate and leucovorin, isoniazid, rifampin and ethambutol, dapsone and rifampicin, erythromycin and rifampicin, clotrimazole and nystatin, amphotericin B and flucytosine, hydrochlorothiazide and amiloride, hydrochiorothiazide and spironolactone, hydrochlorothiazide and captopril, polythiazide and reserpine. Moreover, instead of adding a single plasticizer, a combination of two or more plasticizers could be added to obtain a formulation with the desired consistency and hydrophilicity or hydrophobicity. An example of a combination of plasticizer is acetyl triacetyl citrate (ATEC), n-methyl pyrrolidone (NMP) and a vegetable oil such as sesame oil, olive oil safflower oil sunflower oil cottonseed oil or almond oil.

Example 22

Biodegradable vehicle could be prepared by the procedures shown in Examples 1–20. Instead of adding a single biologically active agent, a combination of two or more biologically active agents could be incorporated together in the said delivery system. Examples of some of the combinations of the biologically active agents include levonorgestrel and ethinyl estradiol, trimethoprim and sulfamethoxazole, trimetrexate and leucovorin, isoniazid, rifampin and ethambutol dapsone and rifampicin, erythromycin and rifampicin, clotrimazole and nystatin, amphotericin B and flucytosine, hydrochlorothiazide and amiloride, hydrochlorothiazide and spironolactone, hydrochlorothiazide and captopril, polythiazide and reserpine. Moreover, instead of adding a single plasticizer, a combination of two or more plasticizers could be added to obtain a formulation with the desired consistency and hydrophilicity or hydrophobicity. An example of a combination of plasticizer is acetyl triacetyl citrate (ATEC), n-methyl pyrrolidone (NMP) and a vegetable oil such as sesame oil, olive oil safflower oil, sunflower oil, cottonseed oil or almond oil.

Example 23

Biodegradable vehicle could be prepared by the procedures shown in Examples 1–20. The vehicle could be loaded in a pharmacy or in an operating room by the health practitioner (a pharmacist, surgeon, nurse), just prior to administration to the patient, with an appropriate quantity of an antitumor agent and injected directly into a solid tumor or at a site from where a solid tumor has been surgically removed.

Example 24

A similar treatment can be offered to patients with brain tumors where the biodegradable vehicle prepared by the methods shown in examples 1–20 and loaded with an appropriate quantity of an antitumor agent can be injected, implanted or applied directly at the site in the brain from where the tumor has been removed.

Example 25

The biodegradable vehicle prepared as shown in examples 1–20 and loaded with a BAS such as an antibiotic an anti-inflammatory agent, a local anesthetic or analgesic, or combinations thereof can also be used in surgeries where appropriate quantities of the BAS, can be blended in the biodegradable vehicle by the surgeon in an operating room, and the resulting mixture can then be injected, implanted, smeared or applied at the site of surgery to minimize the chances of localized infections or inflammation and reduce pain respectively, due to surgery.

Example 26

In the case of orthopedic surgery, a biodegradable vehicle prepared by the method shown in examples 1–20 and loaded with an antibiotic can be injected, implanted, applied or smeared near or at the site of surgery. High concentrations of the antibiotic at the site of surgery can prevent infections. Moreover, the BAS delivery system need not be removed from the site of administration because of the biodegradable nature of the system.

Example 27

The biodegradable vehicle prepared with the methods described in examples 1–20 and loaded with bone growth promoting agents such as calcium sulfate, calcium carbonate, calcium phosphate or hydroxyapatite can be injected, implanted, applied or smeared at an appropriate site where it is needed following bone surgery.

Example 28

The biodegradable vehicle prepared with the methods described in examples 1–20 and loaded with a low molecular weight heparin can also be used to treat conditions such as deep venous thrombosis (DVT) in trauma or surgical patients.

Example 29

For pulsatile or intermittent delivery of BAS such as vaccines, the biodegradable vehicle prepared with the methods described in examples 1–20 can be prepared with blends of varying molecular weights of polymers or copolymers, or with blends of copolymers of varying copolymer ratios such as 50/50 PLGA and 85/15 PLGA or 100% PLA and 25/75 PLGA, or blends of different types of biodegradable polymers with varying hydrophobicity or lipophilicity or crystallinity such as 1:1 of PLA:PCL or 1:3 of PLA:PCL or 1:1 of 50/50 PLGA:PCL.

REFERENCES

Billmeyer, F., Jr. Textbook of Polymer Science, John Wiley and Sons, New York, 1984, p. 472.
Brem et al., J. Neurosurgery, 74:441–446, 1991.
Barrows T. Degradable implant materials: a review of synthetic absorbable polymers and their applications. Clinical materials., 1:233–257, 1986.
Cowsar D R, Dunn R L. Biodegradable and non-biodegradable fibrous delivery systems, in: Longacting Contraceptive Delivery Systems, (Zatuchni G I, Goldsmith A, Shelton J D and Sciarra J J, eds.), Harper & Row, Publishers, Philadelphia, pp. 145–148, 1984.
Dunn et al., U.S. Pat. No. 4,938,763.
Dunn et al., U.S. Pat. No. 5,324,519.
Dunn et al., U.S. Pat. No. 5,324,520.
Dunn et al., U.S. Pat. No. 5,278, 201.
Dunn et al., U.S. Pat. No. 5,340,849.
Dunn et al., U.S. Pat. No. 5,368,859.
Dunn et al., U.S. Pat. No. 5,599,552.
Dunn et al., U.S. Pat. No. 5,487,897.
Eenink M J D, Maassen G C T, Sam A P, Geelen J A A, van Lieshout J B J M, Olijslager J, de Nijs H, and de Jager E. Development of a new long-acting contraceptive subdermal implant releasing 3-ketodesogeatrel. Proceedings of the 15th International Symposium on Controlled Release of Bioactive Materials, Controlled Release Society, Lincolnshire, Ill. pp. 402–403, 1988.
Harrigan S E McCarthy D A, Reuning R and Thies C. Midl. Macromol. Monograph, 5:91–100, 1978.
Jackanicz T M, Nash H A, Wise D L and Gregory J B. Polylactic acid as a biodegradable carrier for contraceptive steroids. *Contraception*, 8:227–233, 1973.
Martin, A., Physical Pharamcy, Lea and Febiger, Philadelphia, 1993, p. 588.
Mason N S, Gupta D V S, Keller, D W, Youngquist R S, and Sparks R F. Biomedical applications of microencapsulation, (Lim F, ed.), CRC Press Inc., Florida, pp. 75–84, 1984.
Mathiowitz E, Leong K and Langer R Macromolecualr drug release from bioerodible polyanhydride microspheres, in: Preceedings of the 12th International Symposium on Controlled Release of Bioactive Materials, (Peppas N and Haluska R, eds.), pp. 183, 1985.
Pitt C G, Gratzl M M, Jeffcoat M A, Zweidinger R and Schindler A. Sustained drug delivery systems II: Factors affecting release rates from poly($\square$-caprolactone) and related biodegradable polyesters. *J. Pharm. Sci.* 68(12):1534–1538, 1979.
Sanders L M, Burns R, Bitale K and Hoffiman P. Clinical performance of nafarelin controlled release injectable: influence of formulation parameters on release kinetics and duration of efficacy. Proceedings of the International Symposium on Controlled Release and Bioactive Materials, 15:62–63, 1988.
Schindler A, Jeffcoat R, Kimmel G L, Pitt C G, Wall M E and Zwelinger R. in: Contemporary Topics in Polymer Science, (Pearce E M and Schaefgen J R, eds.), Vol. 2, Plenum Publishing Corporation, New York, pp. 251–289, 1977.
Sidman K R, Schwope A D, Steber W D, Rudolph S E, Paulin S B. Biodegradable, implantable sustained release systems based on glutamic acid copolymers. *J Membr. Sci.*, 7:277–291, 1980.
Woodland J H R, Yolles S, Blake A B, Helrich M and Meyer F J. Long-acting delivery systems for narcotic antagonist. I. *J Med. Chem.*, 16:897–901, 1973.

What is claimed is:

1. A method for the formulation of a biodegradable system comprising mixing:
(a) at least one biodegradable polymer or copolymer, said polymer or copolymer selected from the group consisting of homopolymers or copolmers of polyesters, polyorhoesters, polylactides, polyglycolides, polycaprolactones, polyhydroxybutyrates, polyhydroxyvalerates, polyamino acids, pseudopolyamino acids, polyamides and polyanhydrides;
(b) at least two plasticizers, wherein at least one plasticizer is hydrophilic and at least one plasticizer is hydrophobic; and
(c) at least one biologically active substance; to produce a biologically active substance-loaded biodegradable vehicle.

2. The method of claim 1 wherein said plasticizers are selected from the group consisting of citrates, phthalates, glycol ethers, n-methyl pyrrolidone, 2 pyrrolidone, propylene gycol, glycerol, glyceryl dioleate, ethyl oleate, benzylbenzoate, glycofurol sorbitol, sucrose acetate isobutyrate, butyryltri-n-hexyl-citrate, acetyltri-n-hexyl citrate, sebacates, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PECs), vegetable oils obtained from seeds, flowers, fruits, leaves, stem or any part of a plant or tree including cotton seed oil, soy bean oil, almond oil, sunflower oil peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

3. The method of claim 1 wherein said biologically active substance is a solid, liquid, semisolid or gas.

4. The method of claim 3 wherein said biologically active agent is a solid, wherein said solid is:
   (a) crystalline, amorphous, granular; or
   (b) granulated with or without added excipient or excipients; or
   (c) encapsulated in an appropriate encapsulating material such as a polymer, a wax or blends thereof; or
   (d) a matrix wherein the biologically active agent is uniformly distributed throughout the matrix prepared with blends of inert excipient or excipients.

5. The method of claim 3 wherein said biologically active agent is:
   (a) a liquid; or
   (b) a solid, liquid or a gas dissolved in a liquid vehicle or mites of liquid vehicles; or
   (c) solid suspended in a liquid vehicle or mixtures of vehicles; or
   (d) liquid emulsified in a liquid vehicle or mixtures of vehicles.

6. The method of claim 3 wherein said biologically active agent is:
   (a) a semisolid; or
   (b) a solid or a gas dissolved or dispersed in a semisolid vehicle or vehicles.

7. The met of claim 1 wherein said biologically active agent is selected from a group consisting of steroids, hormones, antipsychotic agents, agents that act on the central nervous system (CNS-agents), fertility regulating agents, antibodies, antigens, anesthetics, analgesics, antibiotics, antiviral agents, antineoplastic agents, antifungal agents, cavity and infection preventing agents, cardiovascular agents, antiinflammatory agents, vasodilators, brochiodilators, alkaloids, peptides and proteins, vaccines, growth promoting agents, natural tissues such as bones or agents derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues.

8. The method of claim 1 comprising at least two biodegradable polymers.

9. The method of claim 1 wherein said biologically active substance-loaded biodegradable vehicle comprises at least two biologically active substances.

10. The method of claim 9 wherein said biologically active agents are selected from a group consisting of steroids, hormones, antipsychotic agents, agents that act on the central nervous system (CNS-agents), fertility regulating agents antibodies, antigens, anesthetics, analgesics, antibiotics, antiviral agents, antineoplastic agents, antifungal agents, cavity and infection preventing agents, cardiovascular agents, antiinflammatory agents, vasodilators, brochiodilators, alkaloids, peptides and proteins, vaccines, growth promoting agents, natural tissues such as bones or agents derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues.

11. The method of claim 9 wherein said biologically active substance is a solid, liquid, semisolid or gas.

12. The method of claim 11 wherein said biologically active agent is a solid, wherein said solid is:
   (a) crystalline, amorphous, granular; or
   (b) granulated with or without added excipient or excipients; or
   (c) encapsulated in an appropriate encapsulating material such as a polymer, a wax or blends thereof; or
   (d) a matrix wherein the biologically active agent is uniformity distributed throughout the matrix prepared with blends of inert excipient or excipients.

13. The method of claim 11 wherein said biologically active agent is:
   (a) a liquid; or
   (b) a solid, liquid or a gas dissolved in a liquid vehicle or mixtures of liquid vehicles; or
   (c) solid suspended in a liquid vehicle or mixtures of vehicles; or
   (d) liquid emulsified in a liquid vehicle or mixtures of vehicles.

14. The method of claim 11 wherein said biologically active agent is
   (a) a semisolid; or
   (b) a solid or a gas dissolved or dispersed in a semisolid vehicle or vehicles.

15. A method for enhancing the stability of the formulation of a biodegradable system comprising mixing:
   (a) at least one biodegradable polymer or copolymer, said polymer or polymer selected from the group consisting of homopolymers or copolymers of polyesters, polyorthoesters, polylactides, polyglycolides, polycaprolactones, polyhydroxybutyrates, polyhydroxyvalerates, porno acids, pseudopolyamino acids, polyamides and polyanhydrides;
   (b) at leas two plasticizers, wherein at least one plasticizer is hydrophilic and at least one plasticizer is hydrophobic; and
   (c) at least one biologically active substance; to produce a biologically active substance-loaded biodegradable vehicle.

16. The method of claim 15 wherein said plasticizers are selected from the group consisting of citrates, phthalates, glycol ethers, n-methyl pyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyltri-n-hexyl citrate, sebacates, dipropylene glycol methyl ether acetate (DPM acetate), propylene carbonate, propylene glycol laurate, propylene glycol captylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

17. The method of claim 15 wherein said biologically active agent is selected from a group consisting of steroids, hormones, antipsychotic agents, agents that act on the central nervous system (CNS-agents), fertility regulating agents antibodies, antigens, anesthetics, analgesics, antibiotics, antiviral agents, antineoplastic agents, algal agents, cavity and infection preventing agents, cardiovascular agents, antinflammatory agents, vasodilators, brochiodilators, alkaloids, peptides and proteins, vaccines, growth promoting agents, natural tissues such as bones or agents derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues.

18. The method of claim 15 wherein said biologically active substance is a solid, liquid, semisolid or gas.

19. The method of claim 18 wherein said biologically active agent is a solid, wherein said solid is:
    (a) crystalline, amorphous, granular; or
    (b) granulated with or without added excipient or excipients; or
    (c) encapsulated in an appropriate encapsulating material such as a polymer, a wax or blend thereof; or
    (d) a matrix wherein the biologically active agent is uniformly distributed throughout the matrix prepared with blends of inert excipient or excipients.

20. The method of claim 15 wherein said biologically active agent is:
    (a) a liquid; or
    (b) a solid, liquid or a gas dissolved in a liquid vehicle or mixtures of liquid vehicles; or
    (c) solid suspended in a liquid vehicle or mixtures of vehicles; or
    (d) liquid emulsified in a liquid vehicle or mixtures of vehicles.

21. The method of claim 15 wherein said biologically active agent is:
    (a) a semisolid; or
    (b) a solid or a gas dissolved or dispersed in a semisolid vehicle or vehicles.

22. The method of claim 15 comprising at least two biodegradable polymers.

23. The method of claim 15 wherein said biologically active substance-loaded biodegradable vehicle comprises at least two biologically active substances.

24. A method for modulating the release characteristics of the biologically active substance in the formulation of a biodegradable system comprising mixing:
    (a) at least one biodegradable polymer or copolymer, said polymer or copolymer selected from the group consisting of homopolymers or copolymers of polyesters, polyorthoesters, polylactides, polyglycolides, polycaprolactones, polyhydroxybutyrates, polyhydroxyvalerates, polyamino acids, pseudopolyamino acids, polyamides and polyanhydrides;
    (b) at least two plasticizers, wherein at least one plasticizer is hydrophilic and at least one plasticizer is hydrophobic; and
    (c) at least one biologically active substance; to produce a biologically active substance-loaded biodegradable vehicle.

25. The method of claim 24 wherein said plasticizers are selected from the group consisting of citrates, phthalates, glycol ethers, n-methyl pyrrolidone, 2 pyrrolidone, propylene glycol glycerol glyceryl dioleate, ethyl oleate, benzylbenzoate, glycofurol, sorbitol sucrose acetate isobutyrate, butyryltri-n-hexyl-citrate, acetyltri-n-hexyl citrate, sebacates, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6dioleate, polyglyceryl-3isostearate, PEG32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

26. The met of claim 24 wherein said biologically active agent is selected from a group consisting of steroids, hormones, antipsychotic agents, agents that act on the central nervous system (CNS-agents), fertility regulating agents, antibodies, antigens, anesthetics, analgesics, antibiotics, antiviral agents, antineoplastic agents, antifungal agents, cavity and infection preventing agents, cardiovascular agents, antiinflammatory agents, vasodilators, brochiodilators, alkaloids, peptides and proteins, vaccines, growth promoting agents, natural tissues such as bones or agents derived therefrom, bone growth promoting agents such as calcium phosphates, calcium sulfate and hydroxyapatites, whole viable cells and cell-in deoxyribonucleic acid (DNA), DNA fragments, ribonucleic acid, and biological tissues.

27. The method of claim 24 wherein said biologically active substance is a solid, liquid, semisolid or gas.

28. The method of claim 27 wherein said biologically active agent is a solid, wherein said solid is:
    (a) crystalline, amorphous, granular; or
    (b) granulated with or without added excipient or excipients; or
    (c) encapsulated in an appropriate encapsulating material such as a polymer, a wax or blends thereof; or
    (d) a matrix wherein the biologically active agent is uniformly distributed throughout the matrix prepared with blends of inert excipient or excipients.

29. The method of claim 27 wherein said biologically active agent is:
    (a) a liquid; or
    (b) a solid, liquid or a gas dissolved in a liquid vehicle or mixtures of liquid vehicles; or
    (c) solid suspended in a liquid vehicle or mixtures of vehicles; or
    (d) liquid emulsified in a liquid vehicle or mix of vehicles.

30. The method of claim 27 wherein said biologically active agent is:
    (a) a semisolid; or
    (b) a solid or a gas dissolved or dispersed in a semisolid vehicle or vehicles.

31. The method of claim 24 comprising at least two biodegradable polymers.

32. The method of claim 24 wherein said biologically active substance-loaded biodegradable vehicle comprises at least two biologically active substances.

33. A method for modulating the dose of a bioactive agent in the formulation of a biodegradable system comprising mixing:

(a) at least one biodegradable polymer or copolymer, said polymer or copolymer selected from the group consisting of homopolymers or copolymers of polyesters, polyorthoesters, polylactides, polyglycolides, polycaprolactones, polyhydroxybutyrates, polyhydroxyvalerates, polyamino acids, pseudopolyamino acids, polyamides and polyanhydrides;

(b) at least two plasticizers, wherein at least one plasticizer is hydrophilic and at least one plasticizer is hydrophobic; and (c) at least one biologically active substance; to produce a biological active substance-loaded biodegradable vehicle.

34. The method of claim 33 wherein said plasticizers are selected from the group consisting of citrates, phthalates, glycol ethers, n-methyl pyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyltri-n-hexyl citrate, sebacates, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearte, glyceryl palmitostearate, and glyceryl triacetate.

35. The method of claim 33 wherein said biologically active agent is selected from a group consisting of steroids, hormones, antipsychotic agents, agents that act on the central nervous system (CNS-agents), fertility regulating agents, antibodies, antigen anesthetics, analgesics, antibiotics, antiviral agents, antineoplastic agents, antifungal agents, cavity and infection preventing agents, cardiovascular agents antiinflammatory agents, vasodilators, brochiodilators, alkaloids, peptides and proteins, vaccines, growth promoting agents, natural tissues such as bones or agents derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues.

36. The method of claim 33 wherein said biologically active substance is a solid, liquid, semisolid or gas.

37. The method of claim 36 wherein said biologically active agent is a solid, wherein said solid is:

(a) crystalline, amorphous, granular; or (b) granulated with or without added excipient or excipients; or (c) encapsulated in an appropriate encapsulating material such as a polymer, a wax or blends thereof; or (d) a matrix wherein the biologically active agent is uniformly distributed throughout the matrix prepared with blends of inert excipient or excipients.

38. The method of claim 36 wherein said biologically active agent is:

(a) a liquid; or (b) a solid, liquid or a gas dissolved in a liquid vehicle or mixtures of liquid vehicles; or (c) solid suspended in a liquid vehicle or mixtures of vehicles; or (d) liquid emulsified in a liquid vehicle or mixtures of vehicles.

39. The method of claim 36 wherein said biologically active agent is:

(a) a semisolid; or (b) a solid or a gas dissolved or dispersed in a semisolid vehicle or vehicles.

40. The method of claim 33 comprising at least two biodegradable polymers.

41. The method of claim 33 wherein said biologically active substance-loaded biodegradable vehicle comprises at least two biologically active substances.

42. A method for modulating the consistency or rheology of the formulation of a biodegradable system comprising mixing:

(a) at least one biodegradable polymer or copolymer, said polymer or copolymer selected from the group consisting of homopolymers or copolymers of polyesters, polyorthoesters, polylactides, polyglycolides, polycaprolactones, polyhydroxybutyrates, polyhydroxyvalerates; polyamino acids, pseudopolyamino acids, polyamides and polyanhydrides;

(b) at least two plasticizers, wherein at least one plasticizer is hydrophilic and at least one plasticizer is hydrophobic; and (c) at least one biologically active substance; to produce a biologically active substance-loaded biodegradable vehicle.

43. The method of claim 42 wherein said plasticizers are selected from the group consisting of citrates, phhalates, glycol ethers, n-methyl pyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyltri-hexyl citrate, sebacates, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil sesame oil, glycerol and PEG esters of acids and fatty acids, polyglyceryl-3-oleate, polyglyceryl-6dioleate, polyglyceryl-3-isostearate, PEG-32 glyceryl laurate, PEG-32 glyceryl palmitostearate, PEG32 glyceryl stearate, glyceryl behenate, cetyl palmitate, glyceryl di and tri stearate, glyceryl palmitostearate, and glyceryl triacetate.

44. The method of claim 42 wherein said biologically active agent is selected from a group consisting of steroids, hormones, antipsychotic agents, agents that act on the central nervous system (CNS-agents), fertility regulating agents, antibodies, antigens, anesthetics, analgesics, antibiotics, antiviral agents, antineoplastic agents, antifungal agents, cavity and infection preventing agents, cardiovascular agents, antiinflammatory agents, vasodilators, brochiodilators, alkaloid, peptides and proteins, vaccines, growth promoting agents, natural tissues such as bones or agent derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues.

45. The method of claim 42 wherein said biologically active substance is a solid, liquid, semisolid or gas.

46. The method of claim 45 wherein said biologically active agent is a solid, wherein said solid is:

(a) crystalline, amorphous, granular; or (b) granulated with or without added excipient or excipients; or (c) encapsulated in an appropriate encapsulating material such as a polymer, a wax or blends thereof; or (d) a matrix wherein the biologically active agent is uniformly distributed throughout the matrix prepared with blends of inert excipient or excipients.

47. The method of claim 45 wherein said biologically active agent is:

(a) a liquid; or (b) a solid, liquid or a gas dissolved in a liquid vehicle or mixtures of liquid vehicles; or (c) solid suspended in a liquid vehicle or mixtures of vehicles; or (d) liquid emulsified in a liquid vehicle or mixtures of vehicles.

48. The method of claim 45 wherein said biologically active agent is:

(a) a semisolid; or (b) a solid or a gas dissolved or dispersed in a semisolid vehicle or vehicles.

49. The method of claim 42 comprising at least two biodegradable polymers.

50. The method of claim 42 wherein said biologically active substance-loaded biodegradable vehicle comprises at least two biologically active substances.

51. A method for modulating the hydrophilicity or hydrophobicity of the formulation of a biodegradable system comprising mixing:

(a) at least one biodegradable polymer or copolymer, said polymer or copolymer selected from the group costing of homopolymers or copolymers of polyesters, polyorthoesters, polylactides, polyglycolides, polycaprolactones, polyhydroxybutyrates, polyhydroxyvalerates, polyamino acids, pseudopolyamino acids, polyamides and polyanhydrides;

(b) at least two plasticizers, wherein at least one plasticizer is hydrophilic and at least one plasticizer is hydrophobic; and (c) at least one biologically active substance; to produce a biologically active substance-loaded biodegradable vehicle.

52. The method of claim 51 wherein said plasticizers are selected from the group consisting of citrates, phthalates, glycol ethers, n-methyl pyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyltri-hexyl citrate, sebacates, dipropylene glycol methyl ether acetate (DPM acetate), propylene carbonate, propylene glycol laurate, propylene glycol caprylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil soy bean oil, almond oil, sunflower oil, peanut oil, sesame oil, glycerol and PEG esters of acids and fatty acids, polyglyceryl-3oleate, polyglyceryl-6-dioleate, polyglyceryl-3-isostearate, PEG32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

53. The method of claim 51 wherein said biologically active substance is a solid, liquid, semisolid or gas.

54. The method of claim 53 wherein said biologically active agent is a solid, wherein said solid is:

(a) crystalline, amorphous, granular; or (b) granulated with or without added excipient or excipients; or (c) encapsulated in an appropriate encapsulating material such as a polymer, a wax or blends thereof; or (d) a matrix wherein the biologically active agent is uniformly distributed throughout the matrix prepared with blends of inert excipient or excipients.

55. The method of claim 53 wherein said biologically active agent is:

(a) a liquid; or (b) a solid, liquid or a gas dissolved in a liquid vehicle or mixtures of liquid vehicles; or (c) solid suspended in a liquid vehicle or mixtures of vehicles; or (d) liquid emulsified in a liquid vehicle or mixtures of vehicles.

56. The method of claim 53 wherein said biologically active agent is:

(a) a semisolid; or (b) a solid or a gas dissolved or dispersed in a semisolid vehicle or vehicles.

57. The method of claim 51 wherein said biologically active agent is selected from a group consisting of steroids, hormones, antipsychotic agents, agents that act on the central nervous system (CNS-agents), fertility regulating agents, antibodies, antigens, anesthetics, analgesics, antibiotics, antiviral agents, antineoplastic agents, antifungal agents, cavity and infection preventing agents, cardiovascular agents, antinflammatory agents, vasodilators, brochiodilators, alkaloids, peptides and proteins, vaccines, growth promoting agents, natural issues such as bones or agents derived therefrom, bone growth promoting agents such as calcium phosphates, calcium sulfate and hydroxyapatites, whole viable cells and cell-lines deoxyribonucleic acid (DNA), DNA fragments, ribonucleic acid, and biological tissues.

58. The method of claim 51 comprising at least two biodegradable polymers.

59. The method of claim 51 wherein said biologically active substance loaded biodegradable vehicle comprises at least two biologically agent substances.

60. A method for modulating the degradation of the formulation of a biodegradable system comprising mixing:

(a) at least one biodegradable polymer or copolymer, said polymer or copolymer selected from the group consisting of homopolymers or copolymers of polyesters, polyorthoesters, polylactides, polyglycolides, polycaprolactones polyhydroxybutyrates, polyhydroxyvalerates, polyamino acids, pseudopolyamino acids, polyamides and polyanhydrides;

(b) at least two plasticizers, wherein at least one plasticizer is hydrophilic and at least one plasticizer is hydrophobic; and (c) at least one biologically active substance; to produce a biologically active substance-loaded biodegradable vehicle.

61. The method of claim 60 wherein said plasticizers are selected from the group consisting of citrates, phthalates, glycol ethers, n-methyl pyrrolidone, 2 pyrrolidone, propylene glycol glycerol, glyceryl dioleate, ethyl oleate, benzylbenzoate, glycofurol, sorbitol, sucrose acetate isobutyrate, butyryltri-n-hexyl-crate, acetyltri-hexyl citrate, sebacates, dipropylene glycol methyl ether acetate (DPM acetate), propylene carbonate, propylene glycol laurate; propylene glycol caprylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

62. The method of claim 60 wherein said biologically active agent is selected from a group consisting of steroids, hormones, antipsychotic agents, agents that act on the central nervous system (CNS-agents), fertility regulating agents, antibodies, antigens, anesthetics, analgesics, antibiotics, antiviral agents, antineoplastic agents, antifungal agents, cavity and infection preventing agents, cardiovascular agents, antiinflammatory agents, vasodilators, brochiodilators, alkaloids, peptides and proteins, vaccines, growth promoting agents, natural tissues such as bones or agents derived therefrom, bone growth promoting agents such as calcium phosphates, calcium sulfate and hydroxyapatites, whole viable cells and cell-lines, deoxyribonucleic acid (DNA), DNA fragments, ribonucleic acid, and biological tissues.

63. The method of claim 60 wherein said biologically active substance is a solid, liquid, semisolid or gas.

64. The method of claim 63 wherein said biologically active agent is a solid, wherein said solid is:

(a) crystalline, amorphous, granular; or (b) granulated with or without added excipient or excipients; or (c) encapsulated in an appropriate encapsulating material such as a polymer, a wax or blends thereof; or (d) a matrix wherein the biologically active agent is uniformity distributed throughout the matrix prepared with blends of inert excipient or excipients.

65. The method of claim 63 wherein said biologically active agent is:

(a) a liquid; or (b) a solid, liquid or a gas dissolved in a liquid vehicle or mixtures of liquid vehicles; or (c) solid suspended in a liquid vehicle or mixtures of vehicles; or (d) liquid emulsified in a liquid vehicle or mixtures of vehicles.

66. The method of claim 63 wherein said biologically active agent is:

(a) a semisolid; or (b) a solid or a gas dissolve or dispersed in a semisolid vehicle or vehicles.

67. The method of claim 60 comprising at least two biodegradable polymers.

68. The method of claim 60 wherein said biologically active substance-loaded biodegradable vehicle comprises at least two biologically active substances.

* * * * *